United States Patent [19]

Fujiwara et al.

[11] Patent Number: 5,352,599
[45] Date of Patent: Oct. 4, 1994

[54] CO-ENZYME-INDEPENDENT L-SORBOSONE DEHYDROGENASE OF GLUCONOBACTER OXYDANS: ISOLATION, CHARACTERIZATION, AND CLONING AND AUTOLOGUS EXPRESSION OF THE GENE

[75] Inventors: Akiko Fujiwara; Tatsuo Hoshino, both of Kamakura; Masako Shinjoh, Yokohama, all of Japan

[73] Assignee: Hoffmann-La Roche Inc., Nutley, N.J.

[21] Appl. No.: 415,208

[22] PCT Filed: Jan. 9, 1989

[86] PCT No.: PCT/EP89/00010
§ 371 Date: Jun. 11, 1990
§ 102(e) Date: Jun. 11, 1990

[87] PCT Pub. No.: WO89/06688
PCT Pub. Date: Jul. 27, 1989

[30] Foreign Application Priority Data

Jan. 14, 1988 [EP] European Pat. Off. ........ 88100419.6

[51] Int. Cl.$^5$ ..................... C12N 15/53; C12N 15/63; C12N 15/74
[52] U.S. Cl. .................. 435/190; 435/69.1; 435/136; 435/138; 435/172.3; 435/252.3; 435/320.1; 536/23.2; 935/14; 935/60; 935/72
[58] Field of Search .............. 435/69.1-69.9, 435/172.1-172.3, 252.3-252.35, 320.1, 138; 536/27

[56] References Cited

U.S. PATENT DOCUMENTS

| 3,907,639 | 9/1975 | Makover | 435/138 |
| 4,902,617 | 2/1990 | Fujiwara | 435/138 |
| 4,916,069 | 4/1990 | Fujiwara | 435/147 |
| 5,008,193 | 4/1991 | Anderson et al. | 435/183 |
| 5,082,785 | 1/1992 | Manning et al. | 435/252.32 |
| 5,085,993 | 2/1992 | Fujiwara | 435/138 |

FOREIGN PATENT DOCUMENTS 248401 6/1987 European Pat. Off. .
0248400 12/1987 European Pat. Off. .
276832 1/1989 European Pat. Off. .

OTHER PUBLICATIONS

Shaw, K. J., et al., 1979, Genetics 92: 741-747.
Susahi, J., et al., 1985 Agricultural and Biological Chemistry 49: 3017-3022.
Fukuaya, M., et al., 1985, Agricultural and Biological Chemistry 49: 2407-2412.
Daldol, F., et al., 1987, Journal of Molecular Biology 195: 1-24.
Simon, R., et al., 1983 Biol/Technology 1: 784-790.
Krauf, V. C., et al., 1982, Plasmid 8: 45-54.
Berg, D. E., et al., 1983, Bio/Technology, 1(5): 417-435.
Singer, J. T., et al., 1984, Journal of Bacteriology, 157(2): 607-611.
Ohman, D. E., et al., 1985, Journal of Bacteriology 162(3): 1068-1074.
Ehrenshuft, M., et al., 1985, Applied and Environmental Microbiology 50(1): 169-171.

(List continued on next page.)

Primary Examiner—Robert A. Wax
Assistant Examiner—William W. Moore
Attorney, Agent, or Firm—George M. Gould; William H. Epstein

[57] ABSTRACT

A novel coenzyme independent L-sorbosone dehydrogenase originating from a microorganism belonging to the genus Gluconobacter oxydans which acts on L-sorbosone to produce 2-keto-L-gulonic acid.
The enzyme has the following physico-chemical properties:
  a) optimum pH: about 7.0,
  b) optimum temperature: about 30° C. to about 40° C.,
  c) molecular sturucture: consisting of one type of unit having a molecular weight of about 47,500±5,000 as measured by sodium dodecyl sulfate polyacrylamide gel electrophoresis,
  d) thermostability: stable below 30° C., and
  e) inhibition: by Cu$^{2+}$-ions.

18 Claims, 5 Drawing Sheets

OTHER PUBLICATIONS

Allen, C., et al., 1986, Molecular and General Genetics 202: 276–279.
Dolph, P. J., et al., 1988, Journal of Bacteriology 170(2): 865–871.
Makover, et al: Bio. Tech & Bioeng. vol. 17 No. 10, p. 1485 (1775).
Kitamura, et al: Eur J. App. Micro., vol. 2, p. 108 (1975).
Chu, et al: vol. 103, Chem. Abst. No. 25, 207763s (1985).
Inoue, et al. J. Ferment. Tech. vol. 63, No. 1, pp. 104 (1985).
Murooka, J. Bact., vol. 145, No. 1 pp. 358–368 (1981).
Yano, et al. vol. 104, Chem. Abst. No. 1, p. 316 Abstract 48657n (1986).

RESTRICTION MAP OF pVK102

S: Sal I
E: EcoRI
B: BamHI
Bg: BglII
H: HindIII
Sm: SmaI
Tc: TETRACYCLINE RESISTANCE GENE
km: KANAMYCIN RESISTANCE GENE
cos: cos SITE OF λ PHAGE RESTRICTION MAP OF THE SUBCLONES
(a) p7A6Δ2   (b) p7A6Δ3   (c) p7A6Δ4

```
  1 ATG ACC CGT TCC CAG ATC AGG CTT CTC GTC GCG ACC ACC GCC GTC ACC   48
  1 Met Thr Arg Ser Gln Ile Arg Leu Leu Val Ala Thr Thr Ala Val Thr   16

49 GCG CTG CTG GTG GCA GCC GGC TAC CGC GCG GTC GTC TCG CCC GAG GAA   96
 17 Ala Leu Leu Val Ala Ala Gly Tyr Arg Ala Val Val Ser Pro Glu Glu   32

97 GCC CGG CAG ACG GTC GCG GCC GGA ACC GGC CCC CAC CCC GTC CTG CCG  144
 33 Ala Arg Gln Thr Val Ala Ala Gly Thr Gly Pro His Pro Val Leu Pro   48

145 CCG CCC AAC CCC ACC TTC ATG CCC ACG GTC AAC ATC GCC ACG CCC GTC  192
 49 Pro Pro Asn Pro Thr Phe Met Pro Thr Val Asn Ile Ala Thr Pro Val   64

193 GGC TGG CAG GGC ACG CAG GCC CCG ACC CCG GCG GCG GGG CTG GCG GTG  240
 65 Gly Trp Gln Gly Thr Gln Ala Pro Thr Pro Ala Ala Gly Leu Ala Val   80

241 CAT GCC TTC GCC ACC GGC CTG GAC CAC CCC CGC TGG CTG TAC AAG CTG  288
 81 His Ala Phe Ala Thr Gly Leu Asp His Pro Arg Trp Leu Tyr Lys Leu   96

289 CCC AAC GGC GAT ATC CTG GTG GCG GAA TCC GAG TCC CCC GGC ACC GAC  336
 97 Pro Asn Gly Asp Ile Leu Val Ala Glu Ser Glu Ser Pro Gly Thr Asp  112

337 ATC AAG ACG GTG AAG AAC CGC ATC GCC GGC CTG GTC ATG GGC CAG GTC  384
113 Ile Lys Thr Val Lys Asn Arg Ile Ala Gly Leu Val Met Gly Gln Val  128

385 GGC GCG GGC GGA AAA AGC CCC GAC CGC ATC ATC CTG CTG CGC GAT ACC  432
129 Gly Ala Gly Gly Lys Ser Pro Asp Arg Ile Ile Leu Leu Arg Asp Thr  144

433 GAC GGC GAC GGC ATC GCC GAC CAG CGC AGC GTG TTC CTC GAC CAC CTC  480
145 Asp Gly Asp Gly Ile Ala Asp Gln Arg Ser Val Phe Leu Asp His Leu  160

481 TAC TCG CCC TTC GGC ATG GCG CTG GTC GGC GAC ACG CTC TAC GTG GCC  528
161 Tyr Ser Pro Phe Gly Met Ala Leu Val Gly Asp Thr Leu Tyr Val Ala  176

529 AAC GCC AAC GCG CTG GTC CGC TTC CCC TAT CAC GAG GGC GAA ACC CAC  576
177 Asn Ala Asn Ala Leu Val Arg Phe Pro Tyr His Glu Gly Glu Thr His  192

577 ATC GAC GCA CCG GGC GAG AAA GCC GTC GAC CTC CCG GCC GGC TAC AAC  624
193 Ile Asp Ala Pro Gly Glu Lys Ala Val Asp Leu Pro Ala Gly Tyr Asn  208

625 CAC CAC TGG ACC AAG AAC ATC CTG GCC AGC CCG GAC GGC AGC ACC CTC  672
209 His His Trp Thr Lys Asn Ile Leu Ala Ser Pro Asp Gly Ser Thr Leu  224

673 TAC GTG ACC GTC GGC TCC AAC AGC AAC GTC GCC GAC AAC GGC ATG GAG  720
225 Tyr Val Thr Val Gly Ser Asn Ser Asn Val Ala Asp Asn Gly Met Glu  240

721 GTC GAG GAA GGC CGC GCC CGG ATC GAC GGG TTC GAC ATC GCC ACC GGC  768
241 Val Glu Glu Gly Arg Ala Arg Ile Asp Arg Phe Asp Ile Ala Thr Gly  256

769 AAG CTC ACC CCC TAC GCC ACC GGC CTG CGC AAC CCC AAC GAG CTG GCG  816
257 Lys Leu Thr Pro Tyr Ala Thr Gly Leu Arg Asn Pro Asn Glu Leu Ala  272
```

FIG. 4A

```
817  TGG GAG CCC AAG ACC GGC GCC CTG TGG GTC GCA GTG AAC GAA CGC GAC  864
273  Trp Glu Pro Lys Thr Gly Ala Leu Trp Val Ala Val Asn Glu Arg Asp  288

865  GAA ATC GGC AGC GAC CTG GTG CCC GAC TAC ATC ACG GCG GTG AAG GAG  912
289  Glu Ile Gly Ser Asp Leu Val Pro Asp Tyr Ile Thr Ala Val Lys Glu  304

913  GGC GCG TTG TAC GGC TGG CCC TAC AGC TAT TAC GGC CAG CAT GTC GAT  960
305  Gly Ala Phe Tyr Gly Trp Pro Tyr Ser Tyr Tyr Gly Gln His Val Asp  320

961  GTC CGC GTC AAG CCG CAG CGG CCC GAC CTG GTG GCC AGC GCC ATC GCC  1008
321  Val Arg Val Lys Pro Gln Arg Pro Asp Leu Val Ala Ser Ala Ile Ala  336

1009 CCC GAC TAC GCG CTC GGC CCG CAC ACC GCC TGG TTT GGC ATC GCC TTC  1056
337  Pro Asp Tyr Ala Leu Gly Pro His Thr Ala Trp Phe Gly Ile Ala Phe  352

1057 TCG CAG GAC AGC AGC CTG CCC GCG GCC TGG CGC AAT GGC CTG TTC GTC  1104
353  Ser Gln Asp Ser Ser Leu Pro Ala Ala Trp Arg Asn Gly Leu Phe Val  368

1105 GCC CAG CAC GGC TCA TGG AAC CGC AAG CCC AAG AGC GGC TAC CGC GTC  1152
369  Ala Gln His Gly Ser Trp Asn Arg Lys Pro Lys Ser Gly Tyr Arg Val  384

1153 ATC TAC GTC CCC TTC ACC GAC GGC CAC CCC GAC GGC ACC CCC CGC GAG  1200
385  Ile Tyr Val Pro Phe Thr Asp Gly His Pro Asp Gly Thr Pro Arg Asp  400

1201 GTG CTG ACC GGC TTC CTC ACA CAG GAC GAA GAC CAC GCC CAC GGC CGC  1248
401  Val Leu Thr Gly Phe Leu Thr Gln Asp Glu Asp His Ala His Gly Arg  416

1249 CCG GTC GGC CTG GCG CTG GAC AAA TCC GGC GCC CTC CTG GTC GCC GAC  1296
417  Pro Val Gly Leu Ala Leu Asp Lys Ser Gly Ala Leu Leu Val Ala Asp  432

1297 GAT GTC GGC AAC ACC GTG TGG CGC GTC ACC GGC ACG GAC CAG AAG ACC  1344
433  Asp Val Gly Asn Thr Val Trp Arg Val Thr Gly Thr Asp Gln Lys Thr  448

1345 GAC
449  Asp
```

FIG. 4B

CO-ENZYME-INDEPENDENT L-SORBOSONE DEHYDROGENASE OF GLUCONOBACTER OXYDANS: ISOLATION, CHARACTERIZATION, AND CLONING AND AUTOLOGUS EXPRESSION OF THE GENE

The present invention relates to a novel enzyme, namely L-sorbosone dehydrogenase, a process for producing the same and a process for producing 2-keto-L-gulonic acid utilizing said enzyme. Moreover, the present invention relates to genetic engineering techniques which provide an improved method for the cloning and expression of the gene of said enzyme and transformed microorganisms capable of producing 2-keto-L-gulonic acid with high efficiency.

The compound 2-keto-L-gulonic acid (2-KGA) is an important intermediate in the synthesis of ascorbic acid (Vitamin C). Numerous microorganisms are known to produce 2-KGA from D-sorbitol or L-sorbose, for example, members of the genera Acetobacter and Pseudomonas, though levels of 2-KGA produced are less than 6g/L (Japan Patent Publication No. 40,154/1976). Generally the pathway of D-sorbitol to 2-KGA can be illustrated as follows (Makover et al. 1975, Biotechnol. and Bioeng. 17, 1485-1514):

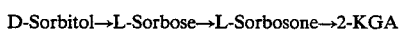

D-Sorbitol→L-Sorbose→L-Sorbosone→2-KGA

Reactions to convert L-sorbosone to 2-KGA using microorganisms are known. 2-KGA production from L-sorbosone using cell free extracts of microorganisms was reported in several prior publications.

In U.S. Pat. No. 3,907,639, microorganisms belonging to the genera Acetobacter, Pseudomonas, Escherichia, Serratia, Bacillus, Staphylococcus, Aerobacter, Alcaligenes, Penicillium, Candida and Gluconobacter were reported to be capable of such a conversion.

Furthermore, Kitamura et al. (Europ. J. Appl. Microbiol., (2) 1, 1975) reported that a L-sorbosone oxidizing enzyme found in *Gluconobacter melanogenes* IFO 3293 required neither coenzyme nor an electron acceptor for the development of its enzyme activity.

However, no disclosure has been made up to now on a purified enzyme having the activity to oxidize L-sorbosone to 2-KGA not depending on coenzymes, e.g. nicotinamide-adenine dinucleotide (NAD) or nicotinamide-adenine dinucleotide phosphate (NADP), etc. It has been found that the purified enzyme isolated from the membrane fraction of cells of specific microorganisms catalyzes the oxidation of L-sorbosone to 2-KGA independently of coenzymes such as NAD and NADP. The present invention has been accomplished based on this finding.

It is an object of the present invention to provide a novel coenzyme independent L-sorbosone dehydrogenase which catalyzes oxidation of L-sorbosone to 2-KGA. It is another object to provide a process for producing said novel L-sorbosone dehydrogenase by a fermentation method. It is also an object to provide an improved process for the production of 2-KGA from L-sorbosone with the aid of said novel L-sorbosone dehydrogenase or a microorganism which produces said enzyme.

Furthermore, another aspect of the object of the present invention is to provide gene engineering techniques which enable the production of said L-sorbosone dehydrogenase by an improved method and also enable the production of 2-KGA from L-sorbosone using said enzyme produced by a recombinant microorganism or using said recombinant microorganism by fermentation. In this respect, DNA comprising the gene encoding said novel L-sorbosone dehydrogenase, vectors and recombinant organisms containing said DNA are also within the scope of the present invention.

It is to be understood that with regard to the partial amino acid sequences given in connection with the DNA, the DNA fragments, the recombinant DNA molecules, the recombinant microorganisms and the processes involved, the functional equivalents of said amino acid sequences, i.e. equivalents which achieve the same goal are also included.

DESCRIPTION OF THE DRAWINGS

FIG. 4 illustrates the DNA sequence encoding L-sorbosone dehydrogenase originated from *Gluconobacter oxydans* IFO 12258.

Figure 1:
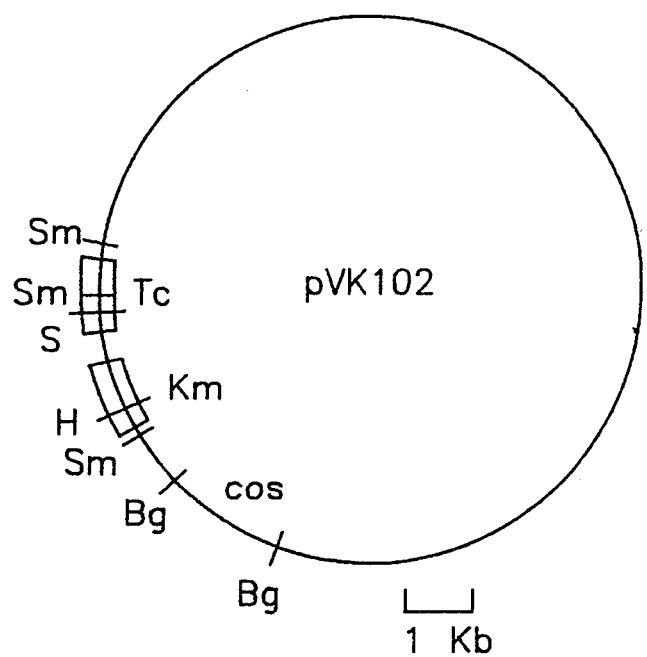
FIG. 1 illustrates the restriction map of the plasmid pVK 102.

The underlined portions indicate partial amino acid sequences also determined by amino acid sequence analysis of peptide fragments of the enzyme protein.

The novel L-sorbosone dehydrogenase of the present invention is characteristic in its independency on coenzymes such as NAD. NADP, flavin mononucleotide (FMN), flavin-adenine dinucleotide (FAD), etc. in the oxidizing reaction from L-sorbosone to 2-KGA.

The properties of the enzyme and the production method may be summarized as follows:

(1) Enzyme activity

The L-sorbosone dehydrogenase of the present invention catalyzes the oxidation of L-sorbosone to 2-KGA in the presence of an electron acceptor according to the following reaction;

L-Sorbosone+Electron acceptor

2-KGA+Reduced electron acceptor

The enzyme does not utilize molecular oxygen as an acceptor. As an acceptor, 2,6-dichlorphenolindophenol (DCIP), phenazine methosulphate, Wurster's blue, ferricyanide, coenzyme Q or cytochrome c can be used.

Enzyme assay was performed at 25° C. by measuring the decrease of absorbance at 600nm of DCIP spectrophotometrically. One unit of enzyme activity was defined as the amount of enzyme which catalyzed the reduction of 1 μmole of DCIP per minute.

The extinction coefficient of DCIP at pH 7.0 was taken as 9.45mM$^{-1}$. The basal reaction mixture is shown below. The mixture was prepared just before the assay.

| Basal mixture: | |
|---|---|
| 0.1 M Potassium phosphate buffer (pH 7.0) containing 0.3% Triton X-100 | 6 ml |
| 2.5 mM DCIP | 0.45 ml |
| H$_2$O | 10.35 ml |

A cuvette with 1cm light path contained 0.4ml of basal mixture, 20μl of 10mM phenazine methosulphate, 10μl of enzyme solution and 20μl of 110mM L-sorbosone solution in a final volume of 0.45ml. A reference cuvette contains all components except the substrate. The reaction was initiated by the addition of the substrate. Enzyme activity was measured as the initial reduction rate of DCIP.

(2) Substrate specificity

The substrate specificity of the enzyme can be determined by the same enzyme assay method as described above under (1) using various substrate solutions. The enzyme of the present invention catalyzes the oxidation of various types of aldehyde compounds as exemplified in Example 3 shown later on.

(3) Physico-chemical properties

The enzyme of the present invention has the following physico-chemical properties:
a) Optimum pH: about 7.0,
b) Optimum temperature about 30° to about 40° C.,
c) Molecular structure: the enzyme consists of one single type of units having a molecular weight of about 47,500±5,000 as measured by sodium dodecyl sulfate polyacrylamide gel electrophoresis,
d) Thermostability: stable below 30° C.,
e) Inhibitor: inhibited by $Cu^{2+}$-ions.

It has to be noted that the optimum temperature range relates to the temperature range where the enzyme exhibits high initial reaction rates, independently of the fact that the enzyme may be decomposed after incubation of longer periods of time at the optimum temperature range.

(4) Production of the enzyme

The L-sorbosone dehydrogenase provided by the present invention can be prepared by cultivating an appropriate microorganism, disrupting the cells and isolating and purifying it from the cell free extract of disrupted cells, preferably from the membrane fraction of the microorganism.

The microorganisms used for the present invention are microorganisms belonging to genus Gluconobacter or mutants thereof. According to the newest classification, all the strains belonging to Gluconobacter fall into the species *Gluconobacter oxydans*.

Morphological and physiological characteristics of the strains belonging to *Gluconobacter oxydans* are described in "Bergey's Manual of Systematic Bacteriology", Vol. I, p. 275–278, 1984 and F. Gosselle et al., International J. System. Bacteriol. Vol. 33, p. 65–81, 1983.

Microorganisms belonging to the genus Gluconobacter which are used in the present invention can be isolated from natural sources or are available from culture collections. The mutants derived thereof may also be used according to the present invention.

The mutants used in the present invention can be obtained by treating a wild type strain with a mutagen such as ultraviolet irradiation, X-ray irradiation, γ-ray irradiation or contact with nitrous acid or other suitable mutagens, or by isolating a clone occurring by spontaneous mutation. These mutations of a wild type strain or a mutant strain thereof may be effected in any of the ways well known per se for this purpose by those skilled in the art. Many of these methods have been described in various publications, see for example, "Chemical Mutagens" edited by Y. Tajima, T. Yoshida and T. Kada, published by Kodansha Scientific Inc., Tokyo, Japan, in 1973.

The mutants according to the present invention can also be obtained by fusion of the strains belonging to the species *Gluconobacter oxydans* and the combination of mutagenesis and/or fusion.

Examples of the strains most preferably used in the present invention are *Gluconobacter oxydans* (listed as melanogenes in the catalogues) IFO 12257, *Gluconobacter oxydans* (listed as melanogenes in the catalogues) IFO 12258 and the like.

The microorganisms may be cultured in an aqueous medium supplemented with appropriate nutrients under aerobic conditions. The cultivation may be conducted at pH of 4.0 to about 8.0, preferably from 5.5 to 7.5. The cultivation period varies depending upon the microorganisms and nutrient medium to be used, it is preferably about 10 to 100 hours. A preferred temperature range for carrying out for the cultivation is from about 10° C. to 40° C., preferably from 25° C. to 30° C.

It is usually required that the culture medium contains nutrients such as assimilable carbon sources, e.g. glycerol. D-mannitol, D-sorbitol, erythritol, ribitol, xylitol, arabitol, inositol, dulcitol, D-ribose, maltose and sucrose, preferably L-sorbose, D-sorbitol or glycerol; digestible nitrogen sources such as organic substances, for example, peptone, yeast extract, soybean meal and corn steep liquor, and inorganic substances, for example, ammonium sulfate, ammonium chloride and potassium nitrite; vitamins and trace elements.

Below, a summary of one of the embodiments for isolation and purification of L-sorbosone dehydrogenase from the microorganisms after the cultivation is described.

(1) Cells are harvested from the fermentation broth by centrifugation.
(2) The cells are suspended in the buffer solution and disrupted by means of a homogenizer, sonicator or treatment with lysozyme and the like to give a disrupted solution of cells.
(3) L-sorbosone dehydrogenase is isolated and purified from the cell free extract of disrupted cells, preferably from the membrane fraction of microorganisms.

The L-sorbosone dehydrogenase provided by the present invention is useful as a catalyst for the production of 2-KGA from L-sorbosone. The reaction should be conducted at pH values of from about 5.0 to about 10.0 in the presence of an electron acceptor, for example, DCIP, phenazine methosulfate, Wurster's blue, ferricyanide, coenzyme Q, cytochrome c and the like, in a solvent such as phosphate buffer, tris-HCl buffer and the like. A preferred temperature range of carrying out the reaction is from about 10° C. to about 50° C. When the pH and temperature a set at about 7.0–8.0 and 30° C., respectively, the reaction usually brings about most preferable results. The concentration of L-sorbosone in a solvent may vary depending on other reaction conditions, but, in general, it is desirable about 10–100g/L, most preferably about 30–40g/L.

In the reaction, the enzyme may also be used in an immobilized state with an appropriate carrier. Any means of immobilizing enzymes generally known to the art may be used. For instance, the enzyme may be bound directly to a membrane, granules or the like of a resin having functional group(s), or it may be bound to the resin through bridging compounds having bifunctional group(s), for example, glutaraldehyde.

Further to the enzyme as such, the process for producing the same and the process for producing 2-KGA using the enzyme outlined above, the present invention encompasses a genetic engineering technique for cloning and expression of the enzyme gene, genetic materials useful for the production of the enzyme, and an improved process for the production of 2-KGA using said genetic materials.

More particularly, the present invention relates to the production of coenzyme independent L-sorbosone dehydrogenase using a recombinant microorganism having introduced a recombinant DNA molecule which contains a gene encoding a polypeptide having the activity of the enzyme, and said recombinant microorganism per se.

The present invention also relates to the gene and the recombinant molecule containing said gene which can be used to construct the above recombinant microorganism.

Furthermore, the present invention relates to a process for producing 2-KGA by contacting L-sorbosone with the enzyme produced from said recombinant microorganism and processes for producing 2-KGA from D-sorbitol, L-sorbose or L-sorbosone by fermentation with the above recombinant microorganism.

Finally, the present invention also relates to a process for producing a transconjugant of the above recombinant microorganism using Gluconobacter strains.

Briefly, the recombinant microorganism utilized in the present invention can be obtained by the following steps:

(1) Constructing a genomic library from the chromosomal DNA of an appropriate strain belonging to the genus Gluconobacter which can produce coenzyme independent L-sorbosone dehydrogenase,
(2) Screening the above genomic library to obtain a clone which expresses the enzyme or its derivative,
(3) If desired, subcloning of the above clone to obtain a subclone which contains a smaller size of the DNA fragment necessary for the expression of the enzyme, and
(4) If desired, reconstruction of the recombinant DNA molecule to enable high productivity.

The materials and the techniques used in the above aspect of the present invention are explained in details as follows:

Cloning of the gene encoding the novel L-sorbosone dehydrogenase and the construction of a recombinant microorganism A) Origin of the gene The gene encoding coenzyme independent L-sorbosone dehydrogenase of the present invention can be cloned from microorganisms belonging to the genus Gluconobacter which can produce said enzyme, preferably from *Gluconobacter oxydans* IFO 12258, Gluconobacter oxydans IFO 12257 or a mutant thereof.

B) Construction of a genomic library

By a procedure well known in the art, the chromosomal DNA isolated from the above origin strain is partially digested with a restriction enzyme such as Sal I, Hind III, Xho I, or EcoR I. The resulting DNA fragments having large molecular size, preferably 15 to 35kb, are collected and ligated with a suitable vector DNA which is digested with an appropriate restriction enzyme and preferably treated with bacterial or calf intestine alkaline phosphatase. As the vector, either a plasmid or phage vehicle can be utilized. In the present invention, the most preferable vector is a cosmid vector, for example, pVK100 (ATCC 37156) or pVK102 (ATCC 37158), or a derivative thereof, i.e. a derivative harboring a cos site of the λ phase, a Mob site, a replication origin of RK2 and one or more marker genes such as antibiotics resistance genes.

Thus, obtained recombinant DNAs on suitable vectors are introduced into a suitable host organism using any of DNA transfer system, for example, transformation, transduction or conjugal mating.

In the present case, the genomic library consisting of the above obtained recombinant DNAs can be suitably constructed in a strain of *Gluconobacter oxydans* as a host by the following procedure:

(1) To obtain a genomic library in a strain of *Gluconobacter oxydans*, the recombinant DNAs are firstly transferred into any strain of *Escherichia coli* to construct a genomic library in *E. coli*. For this purpose, the in vitro packaging system of lamda phage wherein the vector is a cosmid vector can be used. This system using a cosmid vector is suitable for the cloning of a large size DNA. A preferable host for the in vitro packaging system is *E. coli* C600, *E. coli* HB101 or *E. coli* ED8767. The in vitro packaging system is commercially available and can be used according to the manufacturer's instructions. Such a system can be also prepared and used according to the description in the literature, e.g. T. Maniatis et al., Molecular Cloning, A Laboratory Manual, 256–268 (1982), Cold Spring Harbor Press, Cold Spring Harbor, N.Y.

(2) Then, the recombinant DNAs in a strain of *E. coli* as a donor are transferred into a suitable strain of Gluconobacter as a recipient using bi-parental conjugal mating or tri-parental conjugal mating.

When bi-parental conjugal mating is made use of, it is necessary that the donor strain of *E coli* possesses Tra genes on its chromosomal DNA. And when the genomic library in *E. coli* is constructed in a strain not having Tra genes, the recombinant DNAs should be transferred into another *E. coli* strain having Tra genes, *E. coli* S17-1 can be preferably used as such a donor strain. The recombinant DNAs in one strain of *E. coli* can be transferred into the other strain having Tra genes by usual transformation method to construct a new genomic library in *E. coli* which can be used as a donor strain in conjugal mating.

It is also required for the bi-parental conjugal mating that the vehicle which should be transferred by conjugal mating possesses a mob site. The mentioned vectors pVK100, pVK102 or its derivatives having a Mob site are also preferred to construct said vehicle having a Mob site.

Then, each clone of the genomic library in *E. coli* prepared above as the donor is grown in a liquid medium. Simultaneously a strain of Gluconobacter as a recipient is cultured in a test tube containing a suitable medium to log to early stationary phase. The broth of Gluconobacter is then mixed with each broth of *E. coli* at the ratio of about 1:10 to about 10:1. Each mixture is spotted on a nitrocellulose filter on the surface of agar plate of suitable medium for growth of both Gluconobacter and *E. coli*, and the cells on the filter are incubated for 3 hours to 7 days.

(3) The transconjugants can be selected from the mixture of the donor *E. coli*, non-transconjugated Gluconobacter and transconjugated Gluconobacter by appropriate methods, for example, selection by antibiotic resistance and amino acid requirements.

(4) The genomic library in a strain of Gluconobacter can be prepared by collecting appropriate numbers of the above transconjugants.

Transconjugants can be also obtained by tri-parental conjugal mating using E. coli harboring a recombinant plasmid as a donor, E. coli harboring helper plasmid having Tra genes such as RK2 or pRK2013 as a helper and a strain of Gluconobacter as a recipient.

The Gluconobacter strain used as a recipient herein may be any strain belonging to the genus Gluconobacter. Particularly a 2-KGA producer such as *Gluconobacter oxydans* IFO 3292, *Gluconobacter oxydans* IFO 3293 (FERM-P No.8356), *Gluconobacter oxydans* IFO 3294 and their derivatives, a L-sorbosone accumulator such as *Gluconobacter oxydans* OX-4, or a high 2-KGA producer such as *Gluconobacter oxydans* N44-1 or *Gluconobacter oxydans* U-13 (FERM-BP No.1269) and their derivatives can be used. These derivative strains can be obtained by usual mutagenesis as described before.

C) Screening

In general, a genomic library can be screened by using the following methods:

(1) Colony hybridization of a genomic library with an oligonucleotide probe synthesized according to an appropriate amino acid sequence of the enzyme.
(2) Immunological screening of a genomic library by using an antibody against the enzyme as an antigen.
(3) Direct expression screening of a genomic library in a suitable host.

In the present invention, the direct expression screening is preferably used by examining the genomic library constructed in Gluconobacter according to the above explanations. The direct expression screening can be performed by the procedure described hereafter.

Each strain of a genomic library in Gluconobacter is grown on an agar plate, which contains appropriate antibiotics useful as a marker, at 10° to 40° C., preferably at 25° to 30° C., for 1 to 7 days. Thus obtained cells are subjected to a resting-system where cells are suspended in the reaction mixture containing 1 to 5% of L-sorbosone or L-sorbose, 0.3% NaCl and 1% CaCO$_3$, and incubated at 10° to 40° C., preferably at 25° to 30° C., for 1 to 7 days. The resulting reaction mixture is applied to thin layer chromatography to detect positive clones. The positive clones are selected by the accumulation of 2-KGA from L-sorbosone or L-sorbose, or when an L-sorbosone accumulator strain is used, selected by the consumption of L-sorbosone accumulated from L-sorbose.

The above cloned DNA encoding coenzyme independent L-sorbosone dehydrogenase can be characterized by restriction mapping and/or nucleotide sequencing according to methods well known in the art.

D) Stability of the recombinant plasmid

As it is well known in the field of recombinant DNA technology, most of the recombinant microorganisms need some selective pressure such as antibiotics to prevent a loss of the foreign plasmid. However, addition of antibiotics or other drugs to the fermentation broth should be avoided when the products of such a fermentation concern foods, drinks or pharmaceutical products. It should also be avoided for the simplification of the process. Therefore, it has been tried to improve the stability of the recombinant system by particular techniques, e.g. the introduction of a par region into the plasmid, use of a low-copy-number plasmid, or controlled expression of a gene by temperature shift. induction with IPTG (isopropylthiogalactoside), etc.

It is known that the stability of a plasmid is dependent on the combination of a host organism and a plasmid.

It has now been found that the recombinant plasmids which are derived from the plasmids pVK100 and pVK102 are stable in a strain of Gluconobacter in any cultivations, for example. in MB medium, FB medium and the production medium for 2-KGA fermentation as well as pVK100 and pVK102 per se.

Thus, the present invention provides also recombinant plasmids stable in a strain of Gluconobacter, which plasmids are useful for the production of the coenzyme independent L-sorbosone dehydrogenase in Gluconobacter, and for the production of 2-KGA from D-sorbitol, L-sorbose or L-sorbosone.

The stable recombinant expression plasmid of the present invention is characterized in that consisting of at least a DNA fragment derived from the plasmid pVK100 or pVK102, a structural gene to be expressed in a strain of Gluconobacter and, if desired, an expression control region functionally conjugated to said structural gene.

E) Transformed microorganism

The transformant capable of expressing the objective enzyme can be obtained by introducing the above cloned plasmid containing the structural gene of the enzyme into an appropriate host organism. When the plasmid does not have a proper expression control region for the structural gene, an expression plasmid may be reconstructed by introducing a promotor sequence and SD (Shine-Dalgarno) sequence upstream of the structural gene functionally.

In the Example, a DNA fragment containing both an expression control region and the structural gene of the enzyme which was cloned from a strain of Gluconobacter is exemplified. In this case, a plasmid to which the DNA fragment is inserted can express the structural gene of the objective enzyme in a strain of Gluconobacter or an appropriate organism as a host organism.

Production of L-sorbosone dehydrogenase using the transformed microorganism

A) Production and isolation

The transformed microorganism obtained above may be utilized for the production of L-sorbosone dehydrogenase by a fermentation and isolation procedure.

The conditions of the fermentation of the transformant may be selected as usual depending on the host strain. When the host organism is a strain of Gluconobacter, the fermentation condition as described before may also be applied to the transformant.

Isolation of L-sorbosone dehyrogenase produced by the transformant may be carried out by the method well known in the field of protein chemistry.

B) Comparison of the recombinant product with the natural product

The verification of the identity of L-sorbosone dehyrogenase produced by the recombinant organism with the natural one can be carried out by an immunological test, which is well known in the art, as well as the comparison of catalytic properties, such as optimum pH, optimum temperature, molecular weight, thermostability, etc. of the two enzymes.

Thus, the L-sorbosone dehydrogenase produced by the recombinant techniques of the present invention is useful as a catalyst for the production of 2-KGA from L-sorbosone. The production of 2-KGA from L-sorbosone can be effected not only by the said enzyme, but also by the cell free extract, resting cells or the growing cells of the recombinant organism.

The recombinant organism is also useful for the production of 2-KGA from D-sorbitol or L-sorbose in a resting cell system or in a growing cell system.

Typical conditions for the conversion from L-sorbosone to 2-KGA using the isolated recombinant enzyme or the cell free extract are the same as that for the procedure for natural L-sorbosone dehydrogenase described before.

The recombinant organism of the present invention has considerable advantages over its parent organism in the 2-KGA production from D-sorbitol or L-sorbose, when the host organism is a strain of Gluconobacter. The recombinant organism may be cultured in an aqueous medium supplemented with appropriate nutrients under aerobic conditions. In the cultivation, D-sorbitol or L-sorbose used as the starting material can be added into the medium at an appropriate time of fermentation, preferably at the starting point. The concentration range of the starting material, such as D-sorbitol is at a level of 10–400g/L and the culture is maintained at about 10° C. to 40° C., preferably at 25° C. to 30° C. The cultivation may be conducted at pH values of about 4.0–8.0, preferably about 5.5–7.5. The cultivation period varies depending upon the recombinant organisms and nutrient medium to be used, it is preferably about 20 to 200 hours.

The present invention is further illustrated by the following examples.

Example 1

Production of 2-KGA from L-sorbosone by Gluconobacter oxydans strains

G. oxydans strains IF03292, IF03294, IF012257, IF012258, ATCC 9937 and IF03293 (FERM-P No.8356) grown on No.4 (Sg/L of glycerol, 5g/L of yeast extract, 5g/L of MgSO4.7H2O) agar plates were inoculated into 5ml of No.3 B.G medium containing 70g/L of glycerol, 15g/L of yeast extract, 2.Sg/L of MgSO4.7H2O and 10g/L of CaCO3 in a test tube. After the incubation for 3 days at 30° C. on a test tube shaker, one ml of the resulting culture was used to inoculate 50ml of the fresh No.3 B.G medium in a 500ml-Erlenmeyer flask. The flasks were incubated for 3 days at 30° C. on a rotary shaker operating at 180rpm. 20ml of each culture was centrifuged at 5000rpm for 15 minutes. The solids containing cells and remaining CaCO3 were collected, washed twice with 10ml of sterile 0.3% NaCl and suspended in 6ml of the reaction solution containing 3g/L of NaCl, 30g/L of L-sorbosone and 10g/L of CaCO3. The reaction was conducted in a test tube for 23 hours at 30° C. on a tube shaker. The yield of 2-KGA are summarized in Table 1. Evaporation loss during cultivation was not corrected.

Example 2

Isolation and purification of L-sorbosone dehydrogenase from Gluconobacter oxydans IF012258

(1) Cultivation of G. oxydans IF012258

The agar slant culture of G. oxydans IF012258 was inoculated into 5ml of the medium composed of 70g/L of glycerol, 15g/L of yeast extract (Oriental Co., Ltd.) and 2.5g/L of MgSO4.7H2O in a test tube, and incubated at 30° C. for 2 days on a tube shaker (280r.p.m.). Two ml of this culture were transferred to 100ml of the same medium in a 500ml Erlenmeyer flask, and cultivated at 30° C. for 20 hours on a rotary shaker (180r.p.m.). The culture thus prepared was used as an inoculum for a 30L jar fermentor containing 20L of the same medium. The jar fermentor was operated at 30° C., 250r.p.m. (for agitation) and 20L/min. (for aeration) After 40 hours of fermentation, the culture was harvested to collect the cells by centrifugation (8,000r.p.m.). From 20L of broth, 500g (wet weight) of the cells were obtained. The cells were frozen at −20° C. until use.

(2) Preparation of the membrane fraction

The frozen cells of G. oxydans IF012258 (500g, wet weight) were thawed and suspended in 2,500ml of 0.85% NaCl solution. The cell suspension was then homogenized by a Dyno Mill homogenizer (Willy A. Bachofen Co., Basle) in the presence of glass beads (0.1mm in diameter) at 2,000r.p.m. for 4 minutes at 4° C.

The homogenate thus prepared was centrifuged at 1,800 g for 10 minutes to remove the cell debris and glass beads. The resulting supernatant was centrifuged at 80,000 x g for 60 minutes, and then the precipitate was collected as membrane fraction (200g, wet weight).

(3) Solubilization of L-sorbosone dehydrogenase from the membrane fraction

The membrane fraction (200g, wet weight) was suspended in 900ml of 50mM potassium phosphate buffer (pH 7) containing 1% Triton X-100, stirred for 15 hours and centrifuged at 80,000 x g for 1 hour to obtain the supernatant (850ml).

(4) DEAE(diethylamino ethyl)-Toyopearl(polyvinyl type) 650S (Toyo Soda) column chromatography The supernatant (330ml) thus obtained was dialyzed against 20L of 1 mM potassium phosphate buffer containing 0.1% Triton X-100 for 15 hours and applied to a DEAE-Toyopearl 650S column (2.3×40cm), which had been equilibrated with the same buffer. The column was washed with the same buffer, and the enzyme was eluted by a linear gradient of NaCl from 0.0M to 0.4M.

(5) DEAE-Sepharose CL-6B column chromatography

The active fractions from the previous step were combined and dialyzed against 1mM potassium phosphate buffer containing 0.1% Triton X-100 for 15 hours, and then applied to a DEAE-Sepharose CL-6B column (2.5×10cm) equilibrated with the buffer. The column was washed with the same buffer, and the enzyme was eluted by a linear gradient of NaCl from 0.0M to 0.4M.

(6) CM-Sepharose CL-6B column chromatography

The active fractions from the previous step were combined and dialyzed against 1.0mM acetate buffer, pH5.5, containing 0.1% Triton X-100, for 15 hours, and then applied to a CM-Sepharose CL-6B column (2.5×14.5cm) equilibrated with the same buffer. The column was washed with the same buffer, and the enzyme was eluted by a linear gradient of NaCl from 0.0M to 0.4M.

(7) Hydroxyapatite HCA 100S column chromatography

The active fractions from the previous step were combined and dialyzed against 1.0mM potassium phosphate buffer (pH7.0) containing 0.1% Triton X-100, for 15 hours, and then applied to a Hydroxyapatite HCA 100S column (1.7×18cm) equilibrated with the same buffer. The column was washed with the same buffer, and the enzyme was eluted by 10mM potassium phosphate buffer (pH7.0) containing 0.1% Triton X-100.

(8) TSK-GEL Toyopearl HW60S column (polyvinyl type) chromatography

The active fractions from the previous step were combined and concentrated by ultrafiltration using the membrane filter (Diaflo PM-30, Amicon) to a small volume (ca. 1.5ml). Then, the concentrate was applied to a TSK-GEL ToFopearl HW60S column (1.5×80cm) equilibrated with 50 mM potassium phosphate buffer containing 0.1% Triton X-100. The column was developed by the same buffer.

A summary of the purification procedure of membrane-bound L-sorbosone dehydrogenase is shown in Table 2.

Example 3

Properties of L-sorbosone dehydrogenase

(1) Electrophoretic analysis

The purified enzyme with a specific activity of 6.7 unit/mg protein was treated by sodium dodecyl sulfate (SDS) and was analyzed for its purity by SDS-polyacrylamide electrophoresis. It could be proved that the enzyme consists of a single homogeneous subunit with a molecular weight of 47,500±5,000.

(2) Catalytic properties

The purified L-sorbosone dehydrogenase showed its activity only when an electron acceptor such as 2,6-dichlorphenolindo-phenol or phenazine methosulphate was present.

The substrate specificity of the purified enzyme is shown in Table 3. Various types of aldehyde compounds were oxidized. Among them, methylglyoxal was oxidized most efficiently, and the reaction rate was in this case two times higher than that with L-sorbosone.

The apparent Michaelis constant for L-sorbosone was determined to be 16 . 7mM at pH7.0.

As shown in Table 4, the optimum temperature of L-sorbosone dehydrogenase for methylglyoxal oxidation was found to be between 30° C. and 40° C.

The effect of pH on L-sorbosone oxidation is shown Table 5. The enzyme showed its pH optimum at 7.0. The effect of metals on L-sorbosone oxidation was tested. Among the metals tested, it was proved that $Cu2+$ inhibited the enzyme strongly (Table 6). Monoiodoacetic acid moderately inhibited the enzyme as shown in Table 7.

The pH stability of the purified enzyme was examined. After the enzyme was treated in the buffer of various pH's for 48 hours at 4° C., the residual enzyme activity was measured at pH7.0. As shown in Table 8, the enzyme was rather stable over the range of the pH's tested. About one third of the enzyme activity was lost at pH4.0.

The thermostability of L-sorbosone dehydrogenase was examined. As shown in Table 9, about 70% of the enzyme activity was lost by the treatment of 40° C. for 10 minutes.

Example 4

Cloning of G. oxydans IF012258 L-sorbosone dehydrogenase gene

(1) Construction of a cosmid genomic library in E. coli S17-1

(1)-a) Extraction of chromosomal DNA from G. oxydans IF012258

G. oxydans IF012258 was cultivated in 200ml of mannitol broth (MB) (25 g/L of mannitol, 3 g/L of bactopeptone, 5g/L of yeast extract) for 48 hours at 30° C. The cells were collected by centrifugation, washed with 100ml of Tris (10mM)-EDTA (1mM) buffer and resuspended in 50ml of Tris (10mM)-EDTA (20mM) buffer.

The cell suspension thus prepared was treated with 2ml of the lysozyme solution (10mg/ml) at 37° C. for 30 minutes followed by the treatment with pronase (4000 units) at 37° C. for 30 minutes and 10ml of 5% SDS at 37° C. for 1 hour. At this point, a clear lysate was obtained. The DNA was extracted with 60ml of neutral phenol : chloroform containing 4% octanol (1:1) by rotating slowly at 4° C. for 30 minutes. The mixture was centrifuged at 15000rpm for 15 minutes and the supernatant obtained was extracted with 60ml of chloroform : octanol (96:4) by rotating slowly at 4° C. for 10 minutes.

To the 50ml supernatant obtained by centrifugation at 15000rpm for 15 minutes was added 5.0ml of 3M sodium acetate and then slowly 55ml of cold ethanol. The crude DNA was obtained by winding out with a glass rod, which was then treated with RNase $T_1$ and A (37° C., 30 minutes) and pronase (37° C., 30 minutes) again. The phenol and chloroform extractions were repeated to obtain pure chromosomal DNA.

(1)-b) Preparation of the vector plasmid

A cosmid vector, pVK102 (V. C. Knauf et al, Plasmid 8, 45–54, (1982), was prepared from E. coli HB101 harboring pVK102 by the alkaline method (H. C. Birnboim and J. Doly, Nucleic Acids Research, 7, 1513–1523, 1979). The restriction map is illustrated in FIG. 1.

(1)-c) In vitro packaging

The total chromosomal DNA of G. oxydans IF012258 prepared in (1)-a) was partially digested with Sal I (Takara Shuzo Co., Ltd.). The resulting fragments of 15kb to 35kb were isolated from agarose by gel electrophoresis. Plasmid pVK102 (ATCC 37158) prepared in (1)-b) was completely digested with Sal I and dephosphorylated with calf intestine alkaline phosphatase (Boehringer Mannhelm GmbH). The DNA fragments of 15kb to 35kb and the linear pVK102 DNA were ligated with T4 DNA ligase (Takara Shuzo Co., Ltd.).

The ligated fragments were used for the in vitro packaging using a packaging kit (Amersham International plc). The resulting phage particles were incubated with E. coli ED8767 (Murray, N. E. et al, Mol. Gen. Genet. 150, 53, 1977). The cell suspension was plated onto LB agar plates containing 50 mg/L kanamycin.

(1)-d) Construction of the genomic library in E. coli S17-1

One thousand colonies with the marker Km'Tc$^s$ on the LB (Luria-broth) agar plates containing 50mg/L kanamycin were scraped and used to prepare a mixture of recombinant plasmids. The plasmid DNAs were used to transform E. coli S17-1 (Sm$^4$ Tra$^+$) (constructed by Simon R. et al, Biotechnology 1, 784–791, 1982).

One thousand and four hundred transformants were picked into microtiter plates containing LB medium with 100μg/ml of streptomycin and 50μg/ml of kanamycin, incubated overnight and stored with 15% glycerol at −80° C. as the genomic library of G. oxydans IFO12258 in E. coli S17-1. The average size of the inserts was 25kb to 30kb.

(2) Conjugal transfer of the cosmid genomic library in E. coli S17-1 into G. oxydans OX-4

The cosmid genomic library of G. oxydans IFO 12258 in E. coli S17-1 was transferred to G. oxydans OX-4 a L-sorbosone accumulating mutant (obtained from G. oxydans IFO 3293 by mutagenesis as described in European Patent Publication No. 213 591) using bi-parental mating between both strains.

Two hundred μl of log phase culture of the recipient G. oxydans OX-4 grown in mannitol broth were mixed with 100μl of log phase culture of every E. coli S17-1 carrying pVK102 with insert DNA individually and spotted onto nitrocellulose filter on the surface of FB (50g/L fructose, 5g/L yeast extract, 5g/L polypeptone) agar plates. The plates were incubated overnight at 30° C. The mixed colonies were streaked onto MB (mannitol broth) containing 10μg/ml polymyxin B and 50μg/ml kanamycin (this medium being termed MPK) agar plates and incubated for 4 days at 30° C. The resulting conjugants were purified by restreaking on MPK agar plates.

(3) Screening of the genomic library in G. oxydans OX-4

Screening was carried out using a mini-resting system. About 1400 strains of G. oxydans OX-4/pVK102 with insert DNA were suspended in the reaction mixture containing 50μl of 3g/L of NaCl, 10g/L of CaC03 and 30g/L of L-sorbose or L-sorbosone individually and incubated for 1 to 5 days at 30° C. Assays for 2-KGA production were performed by a thin-layer chromatography of silica gel. One positive clone, p7A6, was obtained.

(4) Subcloning of p7A6 and characterization of its subclones

Figure 2:
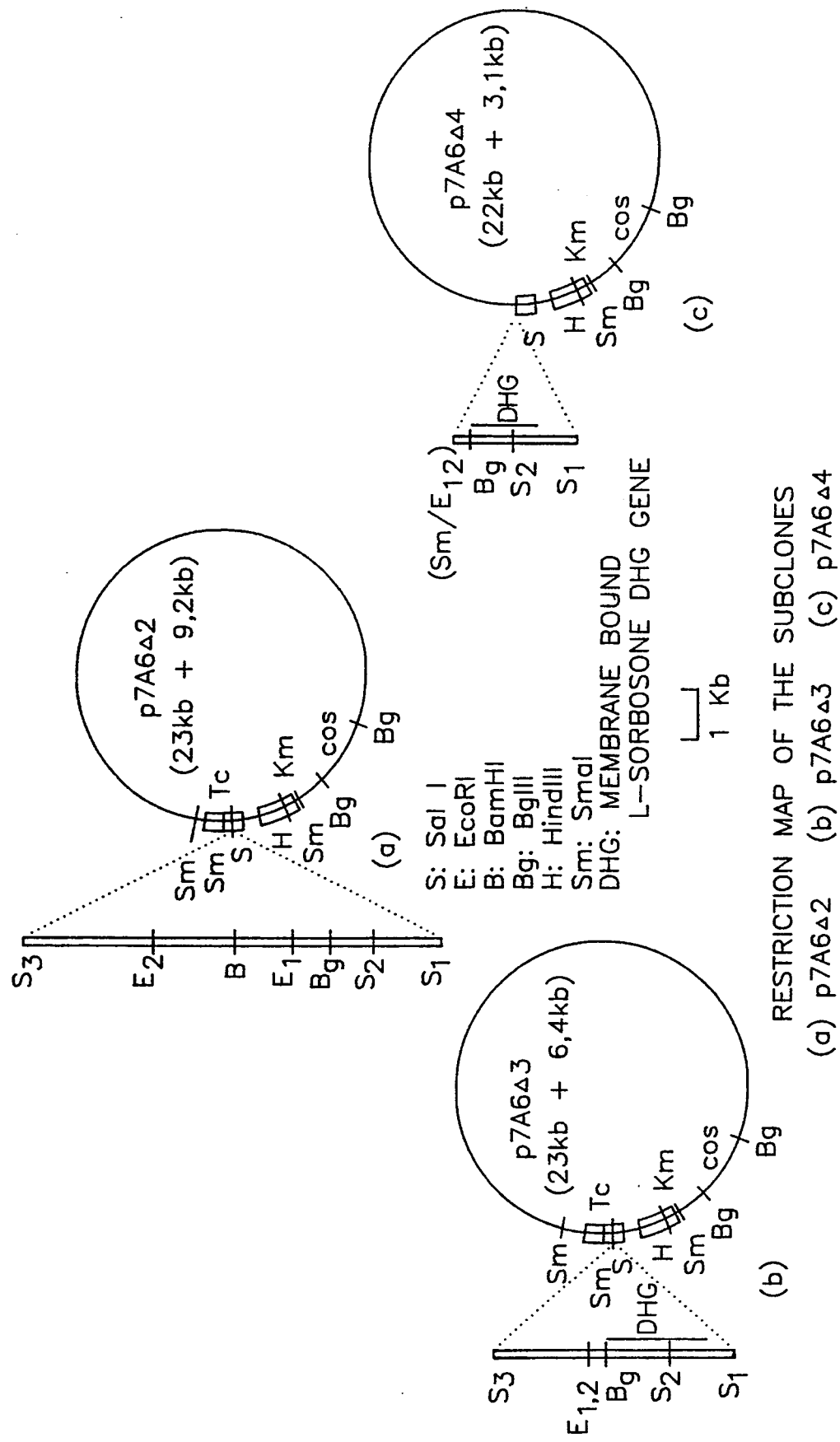
FIG. 2 illustrates the restriction maps of the plasmids of the present invention.
Figure 3:
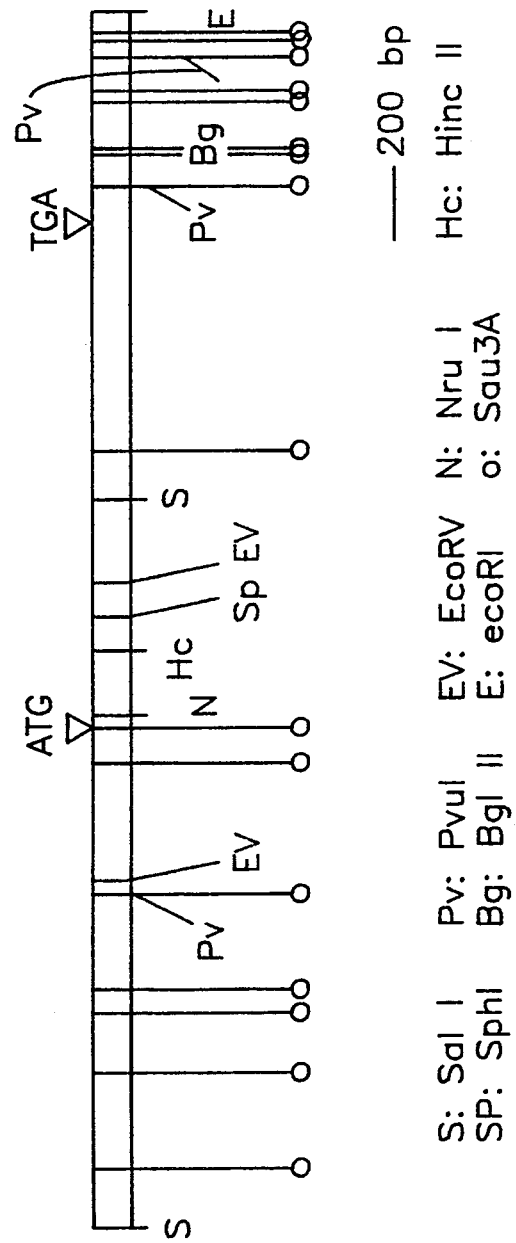
FIG. 3 illustrates the restriction map of a DNA containing the structural gene encoding L-sorbosone dehydrogenase.

The recombinant plasmid p7A6 was prepared by the alkaline method of Birnboim and Doly (Nucleic Acids Research 7, 1513–1523 (1979)) and fragmented with the following restriction enzymes:

EcoRI, EcoRV, HaeIII, HincII, NruI, Sal I, Sau 3A and XhoII (Boehringer Mannheim GmbH), BamHI, BglII, Dra I, Hind III and Sma I (Takara Shuzo Co., Ltd.). EcoRI, HincII, NruI and Sal I digested the insert DNA of p7A6 (25kb) into 8 to 11 fragments. HaeIII, Sau 3A and XhoII generated numerous number of fragments. Sal I was selected for the first step of subcloning.

p7A6 was partially digested with Sal I, ligated with dephosphorylated pVK102 digested with Sal I. The DNA mixture was transferred to E. coli S17-1 by transformation and then to G. oxydans OX-4 by bi-parental conjugation, as described in Example 4.-(2). The smallest subclone, p7A6Δ2, was isolated from the mini-resting screening of 200 conjugants and its size of the insert was 9.2kb (FIG. 2-(a)). A second subcloning was conducted by a deletion of the fragment $E_1$-$E_2$ of p7A6Δ2. p7A6Δ3 (FIG. 2-(b)) thus obtained was further shortened by a deletion of the fragment $E_{\frac{1}{2}}$-Sm$_3$. The resulting subclone, p7A6Δ4 (FIG. 2-(c)), contained a 3.1kb insert in pVK102 with a small deletion of Sm$_2$-Sm$_3$ in the vector DNA. The detailed restriction map of the 3.1kb $S_1$-$S_2E_{\frac{1}{2}}$(SSE) fragment is illustrated in FIG. 3.

(5) Production of recombinant L-sorbosone dehydrogenase and its characterization p7A6 was introduced into G. oxydans N44 1 (such strain being obtainable as outlined for G. oxydans OX-4) from E. coli S17-1/p7A6 by a bi-parental conjugation, as described in Example 4.-(2). The conjugant G. oxydans N44-1/p7A6 was cultivated in 500ml of No.5 medium (100g/L L-sorbose, 15g/L yeast extract, 2.Sg/L MgSO$_4$.7H$_2$O, 0.5g/L glycerol and 20g/L CaCO$_3$) containing 50mg/L kanamycin at 30° C. for 2 days. The cells thus obtained were disrupted by a French Press cell homogenizer in potassium phosphate buffer, pH7.0, treated with DNase in the presence of MgCl$_2$, and centrifuged (6000rpm, 15 min.). The supernatant was centrifuged at 45000rpm (80,000 x g) for one hour to obtain a crude membrane fraction. L-sorbosone dehydrogenase was solubilized from the membrane fraction with 2% Triton X-100 and partially purified through chromato-focusing (i.e. isoelectric chromatography: chromatographic separation method of proteins based on the differences of the isoelectric points of the proteins) and hydroxylapatite column chromatography. SDS-PAGE analysis of the active protein which was detected by active staining and eluted from the PAGE gel exhibited one clear band at 47,500. Thus the molecular weight of the subunit of L-sorbosone dehydrogenase from N44-1/p7A6 was determined to be 47,500, identical with that of L-sorbosone dehydrogenase isolated from G. oxydans IF012258 as described in Example 3-(1). About 300μg of the enzyme protein which had been eluted from SDS-PAGE gel and precipitated with acetone was used to determine the partial amino acid sequence. A fifteen amino acid sequence of the N-terminus was determined as follows:

Met—Thr—Arg—Ser—Gln—Ile—Arg—Leu—Leu—Val—Ala—Thr—Thr—Ala—Val—

Furthermore, the proteolytic digest of the enzyme protein was chromatographed on HPLC.

Several peaks were separately collected and used to determine the internal amino acid sequences of the protein.

Consequently, 6 partial amino acid sequences were determined as follows:

Arg—Asp—Thr—Asp—Gly—Asp—Gly—Ile—Ala—Asp—Gln—Arg,
Lys—Ala—Val—Asp—Leu—Pro—Ala—Gly—Tyr—Asn,
Arg—Ile—Asp—Arg—Phe—Asp—Ile—Ala—Thr—Gly—Lys,
Arg—Asn—Pro—Asn—Glu—Leu—Ala—Trp—Glu—Pro—Lys—Thr—Gly—

Ala—Leu—Trp—Val—Ala—Val—Asn—Glu—Arg,
Lys—Ser—Gly—Tyr—Arg—Val—Ile—Tyr—Val—Pro—Phe—Thr—
Asp—Gly—His—Pro—Asp—Gly—Thr—Pro—Arg, and
Arg—Val—Thr—Gly—Thr—Asp—Gln—Lys.

The allocation of these sequences on the L-sorbosone dehydrogenase is indicated by the underlined portions in FIG. 4.

The enzyme protein purified from the recombinant organism G. oxydans N44-1/p7A6 was also found to be identical with that of G. oxydans IFO12258 immunologically.

(6) Sequencing of the SSE (SalI-SalII-EcoRI DNA-fragment containing L-sorbosone dehydrogenase gene Various fragments obtained from the SSE fragment (3.1kb) illustrated in FIG. 3 were further subcloned into the vector M13mp8 and M13mp9 (Messing, J. and Viera, J. Gene, 19, 269–276, 1982) and sequenced using the commercial sequencing kit (Amersham International plc) on both strands. Stepwise deletion (cutting off) with exonuclease III (Takara Shuzo Co., Ltd., Kilo sequencing kit) was employed.

7-Deaza-dGTP (2'-deoxyguanosine -5'-triphosphate) (Boehringer Mannhelm GmbH) was used in place of dGTP. The N-terminus amino acid sequence of the enzyme protein was confirmed on the DNA sequence of the SSE fragment as follows:

```
5' ATG ACC CGT TCC CAG ATC AGG CTT CTC GTC GCG ACC ACC GCC
   GTC 3

Met Thr Arg Ser Gln Ile Arg Leu Leu Val Ala Thr Thr Ala
   Val
```

The open reading frame of 1347bp was found and its DNA sequence of the structure gene and amino acid sequence deduced from the DNA sequence are shown in FIG. 4.

Example 5

Production of 2-KGA from L-sorbosone by contacting purified *Gluconobacter oxydans* IFO12258 membrane-bound L-sorbosone dehydrogenase The reaction mixture containing 100ml of purified membrane-bound L-sorbosone dehydrogenase (total activity, 1.30 units), 50ml of 0.5M potassium phosphate buffer (pH 7.0), 50ml of 10% L-sorbosone solution, 10ml of 0.2M phenazine methosulfate solution and 290ml of water was incubated at 30° C. with gentle shaking. As a result, 2-KGA was formed with the rate of 650mg/hr.

Example 6

Production of 2-KGA from L-sorbosone by recombinant organisms under a resting-system G. oxydans IFO3292, G. oxydans IFO3294, G. oxydans IFO3293, G. oxydans U-13 (FERM-BP No.1269) and their conjugants carrying p7A6Δ4 prepared in the same manner as described in Example 4-(5) were inoculated from MB agar plate into 5ml of No.5 medium and incubated for 48 hours at 30° C. One ml of each culture was transferred to 50ml of the same medium and these were cultivated at 30° C. on a rotary shaker (180rpm) for 48 hours. The remaining calcium carbonate was removed by centrifugation at 500rpm for 5 minutes. The cells were collected, washed twice with 25ml of sterile 3g/L NaCl solution, and suspended in 6ml of 3g/L NaCl solution.

The reaction mixture containing 3g/L NaCl, 36g/L L-sorbosone, 10g/L CaCO₃ and 2ml cell suspension was incubated in a test tube for 4 days at 30° C. with shaking. The amount of 2-KGA accumulated for 1 day or 4 days incubation is shown in Table 10.

Example 7

Production of 2-KGA from L-sorbose by recombinant organisms under a resting-system G. oxydans U-13 (FERM-BP No.1269) and G. oxydans U-13 containing p7A6Δ4 were used for the resting culture as described in Example 6 except that the substrate was 40g/L L-sorbose.

The yield of 2-KGA after 4 days incubation is shown in Table 11.

Example 8

Production of 2-KGA from L-sorbose by recombinant organism under a growing-system Conjugants; G. oxydans N44-1 carrying pVK102 and G. oxydans N44-1 carrying p7A6Δ4. were prepared in the same manner as described in Example 4-(2). Cells of each conjugant were inoculated from kanamycin-containing MB agar plate into 5ml of No.5 medium with or without kanamycin in a test tube and shaken for 48 hours at 30° C. One tenth ml of each culture was transferred into 5ml of fresh No. 5 medium with or without kanamycin in a test tube and shaken for 120 hours at 30° C.

G. oxydans N44-1. as a control, was cultivated in a similar manner except that the cultivation was carried out without kanamycin.

The yield of 2-KGA is shown in Table 12.

Example 9

Stability of recombinant plasmid during 2-KGA fermentation

Cells of transconjugant; G. oxydans N44-1 carrying p7A6Δ4 or G. oxydans N44-1 carrying p7A6w4, were inoculated from kanamycin-containing MB agar plate into 5ml of No. 5 medium without kanamycin in a test tube and shaken for 48 hours at 30° C. (the first cultivation). A 0.1ml aliquot of each broth was transferred into 5ml of fresh No. 5 medium without kanamycin in a test tube and shaken for 48 hours at 30° C. (the second cultivation). The third cultivation was carried out in the same manner as the second cultivation except that the fermentation continued for 120 hours. Six samples were appropriately diluted after the fermentation, spread on MB agar plates and incubated for 5 days at 30° C. The resulting colonies were picked up (50 colonies per one sample). streaked on MB agar plate with and without kanamycin and incubated for 3 days at 30° C.

The stability of the plasmids was calculated as follows:

$$\text{Stability (\%)} = \frac{\text{Number of colonies with kanamycin-resistance}}{\text{Number of colonies picked up (50 colonies)}} \times 100$$

The result is shown in Table 13.

TABLE 1

2-KGA production from L-sorbosone by *G. oxydans* strains

| Strains | | 2-KGA (g/L) |
|---|---|---|
| *G. oxydans* | IF03292 | 7.6 |
| | IF03294 | 6.8 |
| | IF012257 | 28.5 |
| | IF012258 | 30.8 |
| | ATCC9937 | 2.3 |
| | IF03293 (FERM-PNo. 8356) | 2.7 |

The initial concentration of L-sorbosone was 30g/L.

TABLE 2

Purification of L-sorbosone dehydrogenase from *Gluconobacter oxydans* IFO 12258

| Fraction | Total protein (mg) | Total activity (units) | Specific activity (units/ mg protein) | Yield (%) |
|---|---|---|---|---|
| Solubilized fraction | 2772 | — | — | — |
| DEAE-Toyopearl 650S | 440 | 22.8 | 0.05 | 100 |
| DEAE-Sepharose CL-6B | 247.5 | 15.4 | 0.06 | 67.5 |
| CM-Sepharose CL-6B | 4.5 | 10.0 | 2.22 | 43.9 |
| Hydroxyapatite HCA 100S | 2.4 | 6.1 | 2.54 | 2.68 |
| TSK-GEL Toyopearl HW60S | 0.3 | 2.0 | 6.67 | 8.8 |

TABLE 3

Substrate specificity of membrane-bound L-sorbosone dehydrogenase from *G. oxydans* IFO 12258

| Substrate | Relative activity (%) |
|---|---|
| L-Sorbosone | 100.0 |
| Methylglyoxal | 200.0 |
| Glyoxal | 108.0 |
| Glutaraldehyde | 102.7 |
| Glyoxylic acid | 63.2 |
| Glyceraldehyde | 55.3 |
| Glycolaldehyde | 55.3 |
| Propionaldehyde | 29.0 |
| Acetaldehyde | 21.1 |
| L-Sorbose | 0 |
| D-Glucose | 0 |

TABLE 4

Optimum temperature of membrane-bound L-sorbosone dehydrogenase from *G. oxydans* IFO 12258

| Temperature (°C.) | Relative Activity (%) |
|---|---|
| 10 | 40.2 |
| 20 | 61.2 |
| 30 | 100.0 |
| 40 | 100.0 |
| 50 | 85.1 |
| 60 | 0 |

As the substrate, methylglyoxal was used.

TABLE 5

Optimmum pH of membrane-bound L-sorbosone dehydrogenase of *G. oxydans* IFO 12258

| pH | Buffer (0.1 M) | Relative activity (%) |
|---|---|---|
| 6.0 | Potassium phosphate | 46.1 |

TABLE 5-continued

Optimmum pH of membrane-bound L-sorbosone dehydrogenase of *G. oxydans* IFO 12258

| pH | Buffer (0.1 M) | Relative activity (%) |
|---|---|---|
| 6.5 | " | 60.4 |
| 7.0 | " | 100.0 |
| 7.5 | " | 76.2 |
| 8.0 | " | 85.8 |
| 8.0 | Tris-HCl | 82.6 |
| 8.5 | " | 63.5 |

L-Sorbosone was used as a substrate.

TABLE 6

Effect of metal ions on membrane-bound L-sorbosone dehydrogenase of *G. oxydans* IFO 12258

| Metal ion | Concentration (mM) | Relative activity (%) |
|---|---|---|
| None | 0 | 100.0 |
| $Cu^{2+}$ | 10 | 0 |
| $Co^{2+}$ | 10 | 60.8 |
| $Mn^{2+}$ | 10 | 69.5 |
| $Ni^{2+}$ | 10 | 82.6 |
| $Fe^{3+}$ | 10 | 100.0 |
| $Zn^{2+}$ | 10 | 100.0 |
| $Mo^{6+}$ | 10 | 117.0 |

L-Sorbosone was used as the substrate.

TABLE 7

Effect of inhibitors on membrane-bound L-sorbosone dehydrogenase of *G. oxydans* IFO 12258

| Inhibitors | Concentration (mM) | Relative activity (%) |
|---|---|---|
| None | 0 | 100 |
| $NaN_3$ | 25 | 89.4 |
| $ICH_2COOH$ | 10 | 64.3 |

L-Sorbosone was used as the substrate.

TABLE 8 pH stability of memebrane-bound L-sorbosone dehydrogenase of *G. oxydans* IFO 12258

| pH | Buffer | Relative activity (%) |
|---|---|---|
| 4.0 | Acetate | 64 |
| 4.5 | " | 89 |
| 5.0 | " | 89 |
| 5.5 | " | 90 |
| 6.0 | Potassium phosphate | 92 |
| 6.5 | " | 100 |
| 7.0 | " | 100 |
| 7.5 | " | 103 |
| 8.0 | Tris-HCl | 110 |

The purified enzyme was kept at the indicated pH for 48 hours at 4° C., and the residual enzyme activity was measured at pH 7.0. L-Sorbosone was used as the substrate.

TABLE 9

Thermostability of membrane-bound L-sorbosone dehydrogenase of *G. oxydans* IFO 12258

| Temperature (°C.) | Relative activity (%) |
|---|---|
| 4 | 100 |
| 20 | 88.0 |
| 30 | 86.2 |
| 40 | 29.4 |
| 50 | 3.4 |
| 60 | 0 |

The purified enzyme was treated at the indicated temperature for 10 minutes, and the residual enzyme activity was measured at pH 7.0. L-Sorbosone was used as the substrate.

TABLE 10

2-KGA production from L-sorbosone by recombinant organisms under a resting-system

| Strains | | plasmid | 2-KGA* (g/L) 1 day | (g/L) 4 days |
|---|---|---|---|---|
| G. oxydans | IF03292 | None | — | 6.9 |
| | | P7A6Δ4 | — | 32.1 |
| | IF03294 | None | — | 6.2 |
| | | P7A6Δ4 | — | 33.9 |
| | IF03293 | None | — | 2.0 |
| | | P7A6Δ4 | — | 34.2 |
| | U-13 | None | 5.7 | 8.9 |
| | | P7A6Δ4 | 33.3 | 33.7 |

The initial concentration of L-sorbosone was 36 g/L
*Evaporation loss during incubation was corrected.

TABLE 11

2-KGA production from L-sorbose by recombinant organisms under a resting-system

| Strains | plasmid | 2-KGA* (g/L) |
|---|---|---|
| G. oxydans U-13 (FERM-BP No. 1269) | None | 19.0 |
| | p7A6Δ4 | 35.0 |

The initial concentration of L-sorbose was 40 g/L
Loss through evaporation during incubation was corrected.

TABLE 12

2-KGA production from L-sorbose by recombinant organism under a growing-system

| Plasmid | Km* | 2-KGA (g/L) |
|---|---|---|
| pVK102 | + | 55.7 |
| " | − | 53.8 |
| p7A6Δ4 | + | 63.0 |
| " | − | 64.3 |
| — | — | 56.5 |

*kanamycin
Host: G. oxydans N44-1

TABLE 13

Stability* of vector and recombinant plasmid during 2-KGA fermentation (%)

| Plasmid | Km | 1st cultivation 48 hours | 2nd cultivation 48 hours | 3rd cultivation 120 hours |
|---|---|---|---|---|
| pVK102 | — | 96 | 94 | 82 |
| p7A6Δ4 | — | 94 | 100 | 88 |

*Stability (%) = $\frac{\text{Number of colonies with kanamycin-resistance}}{\text{Total number of colonies tested}} \times 100$

We claim:

1. An isolated and purified DNA segment consisting essentially of a region encoding a Gluconobacter, coenzyme independent, L-sorbosone dehydrogenase, said dehydrogenase capable of converting L-sorbosone to 2-keto-L-gulonic acid.

2. The isolated and purified DNA segment according to claim 1, wherein said Gluconobacter coenzyme independent L-sorbosone dehydrogenase has the following partial amino acid sequences:

Met—Thr—Arg—Ser—Gln—Ile—Arg—Leu—Leu—Val—Ala—Thr—Thr—Ala—Val, (N terminal)

Arg—Asp—Thr—Asp—Gly—Asp—Gly—Ile—Ala—Asp—Gln—Arg,

Lys—Ala—Val—Asp—Leu—Pro—Ala—Gly—Tyr—Asn,

Arg—Ile—Asp—Arg—Phe—Asp—Ile—Ala—Thr—Gly—Lys,

Arg—Asn—Pro—Asn—Glu—Leu—Ala—Trp—Glu—Pro—Lys—Thr—Gly—Ala—Leu—Trp—Val—Ala—Val—Asn—Glu—Arg,

Lys—Ser—Gly—Tyr—Arg—Val—Ile—Tyr—Val—Pro—Phe—Thr—Asp—Gly—His—Pro—Asp—Gly—Thr—Pro—Arg, and Arg—Val—Thr—Gly—Thr—Asp—Gln—Lys.

3. The isolated and purified DNA segment, DNA fragment according to claim 1, wherein said region is characterized by restriction map; depicted in FIG. 3.

4. A recombinant Gluconobacter microorganism transformed with a recombinant DNA vector, said vector having a DNA segment consisting essentially of a region encoding a Gluconobacter, coenzyme independent, L-sorbosone dehydrogenase said dehydrogenase capable of converting L-sorbosone to 2-keto-L-gulonic acid.

5. The recombinant microorganism of claim 4, wherein said coenzyme independent L-sorbosone dehydrogenase has the following partial amino acid sequences:

Met—Thr—Arg—Ser—Gln—Ile—Arg—Leu—Leu—Val—Ala—Thr—Thr—Ala—Val, (N terminal)

Arg—Asp—Thr—Asp—Gly—Asp—Gly—Ile—Ala—Asp—Gln—Arg,

Lys—Ala—Val—Asp—Leu—Pro—Ala—Gly—Tyr—Asn,

Arg—Ile—Asp—Arg—Phe—Asp—Ile—Ala—Thr—Gly—Lys,

Arg—Asn—Pro—Asn—Glu—Leu—Ala—Trp—Glu—Pro—Lys—Thr—Gly—Ala—Leu—Trp—Val—Ala—Val—Asn—Glu—Arg,

Lys—Ser—Gly—Tyr—Arg—Val—Ile—Tyr—Val—Pro—Phe—Thr—Asp—Gly—His—Pro—Asp—Gly—Thr—Pro—Arg, and Arg—Val—Thr—Gly—Thr—Asp—Gln—Lys.

6. A recombinant microorganism according to claim 5, which is a Gluconobacter selected from the group consisting of *Gluconobacter oxydans* OX-4/p7A6, *Gluconobacter oxydans* N44-1/p7A6, *Gluconobacter oxydans* N44-1/p7A6Δ4, *Gluconobacter oxydans* U-13/p7A6Δ4, *Gluconobacter oxydans* IFO 3292/p7A6Δ4, *Gluconobacter oxydans* IFO 3293/p7A6Δ4 and *Gluconobacter oxydans* IFO 3294/p7A6Δ4.

7. A recombinant microorganism according to claim 6, which is a transconjugant of a strain belonging to the genus Gluconobacter.

8. A process for producing 2-keto-L-gulonic acid comprising cultivating a Gluconobacter microorganism in a medium comprising a sugar selected from the group consisting of L-sorbose, L-sorbosone and D-sorbitol, wherein said microorganism is transformed with a recombinant DNA vector, said vector having a DNA segment consisting essentially of a region encoding a Gluconobacter, coenzyme independent, L-sorbosone dehydrogenase, said dehydrogenase capable of converting L-sorbosone to 2-L-gulonic acid.

9. The process of claim 8, wherein the sugar is L-sorbosone.

10. A process according to claim 9, wherein said coenzyme independent L-sorbosone dehydrogenase has the following partial amino acid sequences:

Met—Thr—Arg—Ser—Gln—Ile—Arg—Leu—Leu—Val—Ala—Thr—Thr—Ala—Val, (N terminal)

Arg—Asp—Thr—Asp—Gly—Asp—Gly—Ile—Ala—Asp—Gln—Arg,

Lys—Ala—Val—Asp—Leu—Pro—Ala—Gly—Tyr—Asn,

Arg—Ile—Asp—Arg—Phe—Asp—Ile—Ala—Thr—Gly—Lys,

Arg—Asn—Pro—Asn—Glu—Leu—Ala—Trp—Glu—Pro—Lys—Thr—Gly—Ala—Leu—Trp—Val—Ala—Val—Asn—Glu—Arg,

Lys—Ser—Gly—Tyr—Arg—Val—Ile—Tyr—Val—Pro—Phe—Thr—Asp—Gly—His—Pro—Asp—Gly—Thr—Pro—Arg, and Arg—Val—Thr—Gly—Thr—Asp—Gln—Lys.

11. A process according to claim 10, wherein said microorganism is *Gluconobacter oxydans* OX-4/p7A6, *Gluconobacter oxydans* N44-1/p7A6, *Gluconobacter oxydans* N44-1/p7A6Δ4, *Gluconobacter oxydans* U-13/p7A6Δ4, *Gluconobacter oxydans* IFO 3292/p7A6Δ4, *Gluconobacter oxydans* IFO 3293/p7A6Δ4 or *Gluconobacter oxydans* IFO 3294/p7A6Δ4.

12. The process of claim 8, wherein the sugar is L-sorbose.

13. A process according to claim 12, wherein said coenzyme independent L-sorbosone dehydrogenase has the following partial amino acid sequences:

Met—Thr—Arg—Ser—Gln—Ile—Arg—Leu—Leu—Val—Ala—Thr—Thr—Ala—Val, (N terminal)

Arg—Asp—Thr—Asp—Gly—Asp—Gly—Ile—Ala—Asp—Gln—Arg,

Lys—Ala—Val—Asp—Leu—Pro—Ala—Gly—Tyr—Asn,

Arg—Ile—Asp—Arg—Phe—Asp—Ile—Ala—Thr—Gly—Lys,

Arg—Asn—Pro—Asn—Glu—Leu—Ala—Trp—Glu—Pro—Lys—Thr—Gly—Ala—Leu—Trp—Val—Ala—Val—Asn—Glu—Arg,

Lys—Ser—Gly—Tyr—Arg—Val—Ile—Tyr—Val—Pro—Phe—Thr—Asp—Gly—His—Pro—Asp—Gly—Thr—Pro—Arg, and Arg—Val—Thr—Gly—Thr—Asp—Gln—Lys.

14. A process according to claim 13, wherein said microorganism is *Gluconobacter oxydans* OX-4/p7A6, *Gluconobacter oxydans* N44-1/p7A6, *Gluconobacter oxydans* N44-1/p7A6Δ4, *Gluconobacter oxydans* U-13/p7A6Δ4, *Gluconobacter oxydans* IFO 3292/p7A6Δ4, *Gluconobacter oxydans* IFO 3293/p7A6Δ4 and *Gluconobacter oxydans* IFO 3294/p7A6Δ4.

15. The process of claim 8, wherein the sugar is D-sorbitol.

16. The process according to claim 15, wherein said coenzyme independent L-sorbosone dehydrogenase has the following partial amino acid sequences:

Met—Thr—Arg—Ser—Gln—Ile—Arg—Leu—Leu—Val—Ala—Thr—Thr—Ala—Val, (N terminal)

Arg—Asp—Thr—Asp—Gly—Asp—Gly—Ile—Ala—Asp—Gln—Arg,

Lys—Ala—Val—Asp—Leu—Pro—Ala—Gly—Tyr—Asn,

Arg—Ile—Asp—Arg—Phe—Asp—Ile—Ala—Thr—Gly—Lys,

Arg—Asn—Pro—Asn—Glu—Leu—Ala—Trp—Glu—Pro—Lys—Thr—Gly—Ala—Leu—Trp—Val—Ala—Val—Asn—Glu—Arg,

Lys—Ser—Gly—Tyr—Arg—Val—Ile—Tyr—Val—Pro—Phe—Thr—Asp—Gly—His—Pro—Asp—Gly—Thr—Pro—Arg, and Arg—Val—Thr—Gly—Thr—Asp—Gln—Lys.

17. A process according to claim 16, wherein said microorganism is *Gluconobacter oxydans* OX-4/p7A6, *Gluconobacter oxydans* N44-1/p7A6, *Gluconobacter oxydans* N44-1/p7A6Δ4, *Gluconobacter oxydans* U-13/p7A6Δ4, *Gluconobacter oxydans* IFO 3292/p7A6Δ4, *Gluconobacter oxydans* IFO 3293/p7A6Δ4 and *Gluconobacter oxydans* IFO 3293/p7A6Δ4.

18. A method for producing a transconjugant using a microorganism belonging to the genus Gluconobacter as a recipient, comprising contacting said recipient with a donor having a plasmid derived from pVK100 or pVK102, wherein said plasmid contains both a Mob site and cos site, and transferring the plasmid from the donor to the recipient through the use of the Tra gene function.

* * * * *